(12) United States Patent
Li

(10) Patent No.: US 12,740,718 B2
(45) Date of Patent: Sep. 22, 2026

(54) REMOVAL OF MOTION ARTIFACTS IN A PHOTOPLETHYSMOGRAPHY SIGNAL

(71) Applicant: EdgeImpulse Inc., San Jose, CA (US)

(72) Inventor: Yan Li, Victoria (CA)

(73) Assignee: EdgeImpulse Inc., San Diego, CA (US)

( * ) Notice: Subject to any disclaimer, the term of this patent is extended or adjusted under 35 U.S.C. 154(b) by 0 days.

(21) Appl. No.: 18/811,121

(22) Filed: Aug. 21, 2024

(65) Prior Publication Data

US 2026/0053380 A1 Feb. 26, 2026

(51) Int. Cl.

*A61B 5/024* (2006.01)
*A61B 5/00* (2006.01)

(52) U.S. Cl.

CPC ........ *A61B 5/02416* (2013.01); *A61B 5/6824* (2013.01); *A61B 5/721* (2013.01); *A61B 5/7221* (2013.01); *A61B 5/725* (2013.01); *A61B 5/7271* (2013.01); *A61B 2560/0462* (2013.01); *A61B 2562/0219* (2013.01)

(58) Field of Classification Search

CPC ... A61B 5/02416; A61B 5/6824; A61B 5/721; A61B 5/7221; A61B 5/725; A61B 5/7271; A61B 2560/0462; A61B 2562/0219

See application file for complete search history.

(56) References Cited

U.S. PATENT DOCUMENTS

2005/0085735 A1 4/2005 Baker et al.
2010/0298661 A1* 11/2010 McCombie ........ G08B 21/0446 600/587
2012/0283581 A1* 11/2012 Olde .................... A61B 5/4094 600/485

(Continued)

FOREIGN PATENT DOCUMENTS

| | | | |
|---|---|---|---|
| AU | 736060 | B2 | 7/2001 |
| CN | 118141354 | A | 6/2024 |
| EP | 4223216 | A1 | 8/2023 |

OTHER PUBLICATIONS

Peng et al., "Motion Artifact Removal From Photoplethysmographic Signals by Combining Temporally Constrained Independent Component Analysis and Adaptive Filter," BioMedicalEngineering OnLine 2014, 13:50, http://www.biomedical-engineering-online.com/content/13/1/50, 14 pp.

(Continued)

*Primary Examiner* — Hien N Nguyen
(74) *Attorney, Agent, or Firm* — Polsinelli LLP

(57) ABSTRACT

Removal of motion artifacts from photoplethysmography (PPG) signals from a PPG sensor by applying a harmonic notch filter to a PPG signal where positions of the filter notches are based on a period of an accelerometer signal received from an accelerometer sensor in a vicinity of the PPG sensor to yield a first filtered signal; determining a signal quality index (SQI) associated with the PPG signal based on the accelerometer signal; determining an estimated heart rate based on the PPG signal; and applying a harmonic comb filter to the first filtered signal to where the filter peaks are based on the estimated heart rate. The estimated heart rate may be determined according to a confidence level based on SQI. A wearable device may implement the system for removing motion artifacts from PPG signals.

17 Claims, 6 Drawing Sheets

(56) References Cited

U.S. PATENT DOCUMENTS

| | | | | |
|---|---|---|---|---|
| 2016/0022220 | A1* | 1/2016 | Lee | A61B 5/02433 600/479 |
| 2016/0038045 | A1* | 2/2016 | Shapiro | A61B 5/721 600/479 |
| 2016/0051157 | A1* | 2/2016 | Waydo | A61B 5/7246 600/479 |
| 2017/0071545 | A1 | 3/2017 | Ritscher et al. | |
| 2017/0095169 | A1* | 4/2017 | Liu | A61B 5/681 |
| 2017/0095212 | A1* | 4/2017 | Albadawi | A61B 5/112 |
| 2017/0181680 | A1 | 6/2017 | Baek et al. | |
| 2023/0277135 | A1* | 9/2023 | Kibler | G16H 40/63 600/301 |

OTHER PUBLICATIONS

Wang et al., "Elimination of Motion Artifacts in Signal of Photoplethysmography Sensor," Sensors and Materials, vol. 34, No. 9 (2022) 3461-3477, MYU Tokyo, 17 pp.

Lee et al., "Motion Artifact Reduction in Wearable Photoplethysmography Based on Multi-Channel Sensors with Multiple Wavelengths," Pub. Mar. 9, 2020, Sensors 2020, 20, 1493; doi: 10.3390/s20051493, www.mdpi.com/journal/sensors, 14 pp.

Wang et al., "Removal of Motion Artifacts in Photoplethysmograph Sensors during Intensive Exercise for Accurate Heart Rate Calculation Based on Frequency Estimation and Notch Filtering," Pub. Jul. 28, Sensors 2019, 19, 3312; doi:10.3390/s19153312, www.mdpi.com/journal/sensors, 14 pp.

Pollreisz et al., "Detection and Removal of Motion Artifacts in PPG Signals," Mobile Networks and Applications (2022) 27:728-738, Pub. Aug. 8, 2019, https://doi.org/10.1007/s11036-019-01323-6, 11 pp.

Seok, et al., "Motion Artifact Removal Techniques for Wearable EEG and PPG Sensor Systems," Frontiers in Electronics, Pub. May 13, 2021, vol. 2, Article 685513, doi: 10.3389/felec.2021.685513, 17 pp.

International Search Report and Written Opinion—PCT/US2025/039156—ISA/EPO—Nov. 3, 2025.

* cited by examiner

600

700

REMOVAL OF MOTION ARTIFACTS IN A PHOTOPLETHYSMOGRAPHY SIGNAL

TECHNICAL FIELD

This disclosure relates generally to photoplethysmography (PPG), more specifically, to removal of motion artifacts in PPG signals.

BACKGROUND

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
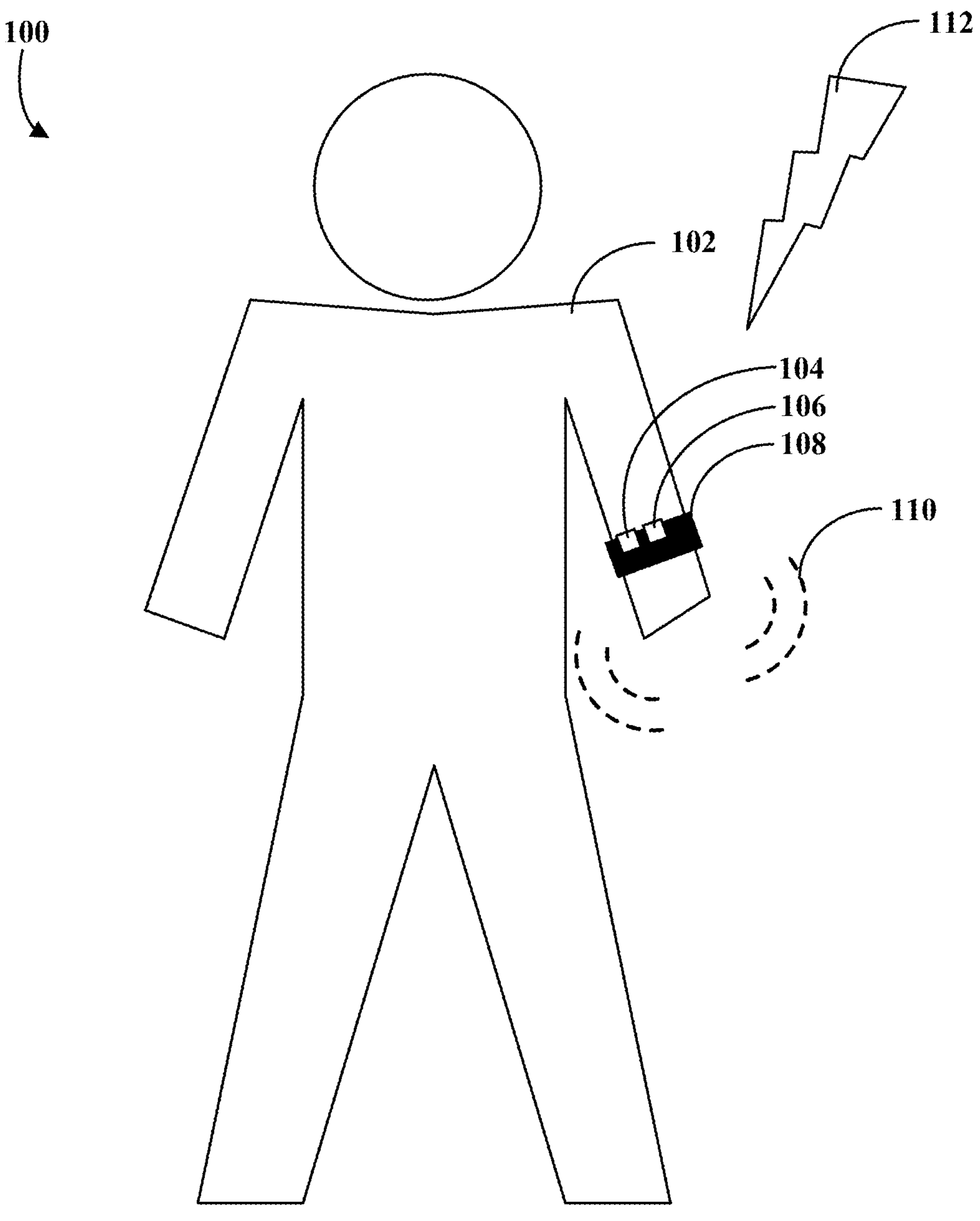
FIG. 1 is a diagram of an example of a PPG sensor encountering motion artifacts.

Photoplethysmography is a non-invasive optical technique used to detect blood volume changes in the microvascular bed of tissue. PPG utilizes a light source, such as a light-emitting diode (LED), and a photodetector, such as a photodiode, placed on the skin to measure variations in light absorption that corresponds to blood flow. PPG is commonly used in wearable health devices, such as fitness trackers and smartwatches, to monitor heart rate, blood oxygen saturation, and other cardiovascular metrics. Its simplicity, cost-effectiveness, and ability to provide continuous monitoring make it a valuable tool in both clinical and consumer health settings.

PPG signals can be contaminated by noise and/or artifacts stemming from physical motion (collectively referred to herein as "motion artifacts"), especially for PPG sensors on wearable devices for fitness and health monitoring where physical movement, such as running or cycling, is expected. For wearable devices that use PPG to monitor heart rate, it is advantageous to reduce such motion artifacts to improve accuracy of heart-rate measurements. However, traditional frequency-dependent filtering tends to be ineffective at removing motion artifacts when the motion artifacts are quasi-periodic with quasi-frequencies that are on the same order of magnitude as the heart rate when expressed in similar units, such as inverse seconds (e.g., cycles per second (Hz), beats per second, etc.) or inverse minutes (e.g., cycles per minute, beats per minute (bpm), etc.). For example, a person's heart rate can range from 60 bpm or less at rest and up to 200 bpm during intense exercise. Similarly, motion artifacts from cycling can range from 20 cycles per minute at a slow pace and around 150 to 180 cycles per minute at a sprint pace. Traditional frequency-dependent filtering to remove signal components in the frequency range of the motion, e.g., cycling, would not only remove those frequency components of the motion artifacts, but would remove those frequency components from the heart rate signal.

The term "quasi-periodic" is used herein to describe a signal that exhibits periodicity, where the period (e.g., one or more frequency components) may change over time. For simplicity, the prefix "quasi" is hereinafter dropped when describing signals that are quasi-periodic and the terms "period," "periodic," "and "frequency" are used to describe such signals.

Embodiments disclosed herein overcome one or more of the challenges described above for improving accuracy of heart-rate measurements from a PPG signal that exhibits motion artifacts, such as a PPG signal acquired via a wearable device (e.g. via one or more sensors mounted on or integrated with a wearable device). The embodiments disclosed herein employ two harmonic filters in sequence, as summarized below.

In some embodiments, a first harmonic filter is a harmonic notch filter, also known as a harmonic rejection filter, implemented as an N-tap finite impulse response (FIR) filter, where $N \geq 2$. The harmonic notch filter removes periodic (e.g., quasi-periodic) motion artifacts from a PPG signal, where the period of the motion artifacts is on the same order of magnitude as the period of the heart-rate signal. In some embodiments, an accelerometer signal is used to identify a dominant frequency of a motion-artifact, and its harmonics.

In some embodiments, a second harmonic filter is a harmonic comb filter, also known as a harmonic enhancement filter, implemented as an M-tap IIR filter, where $M \geq 2$. The harmonic comb filter enhances the frequency components of the heart-rate signal according to a most-recently-determined heart rate, where the frequency of the heart rate signal does not change drastically over a short time frame, such as two seconds.

In some embodiments, the harmonic notch filter and the harmonic comb filter may be considered inverse functions of each other. While the harmonic notch filter and the harmonic comb filter may each comprise more than two taps, it may be advantageous to limit the number of taps to minimize power consumption (or at least to balance power consumption with performance or measurement-accuracy requirements). Minimal power consumption can be advantageous for implementation in wearable devices that may be powered from small or compact batteries. In some embodiments, the harmonic notch filter and the harmonic comb filter are each 2-tap filters ($N=M=2$).

To describe some embodiments in greater detail, reference is first made to examples of hardware and software structures used to implement a system for removing motion artifacts in PPG signals. FIG. 1 is a diagram of an example environment 100 comprising a user 102 wearing a wearable device 108. The wearable device 108 comprises a PPG sensor 104 for measuring a heart rate of the user 102 and an accelerometer sensor 106 for detecting motions 110 of the wearable device 108, which may manifest as motion artifacts detected by the PPG sensor 104. The wearable device 108 may comprise, for example, a watch, a ring, or a cuff.

The wearable device may communicate with other computing devices via a network 112.

Figure 2:
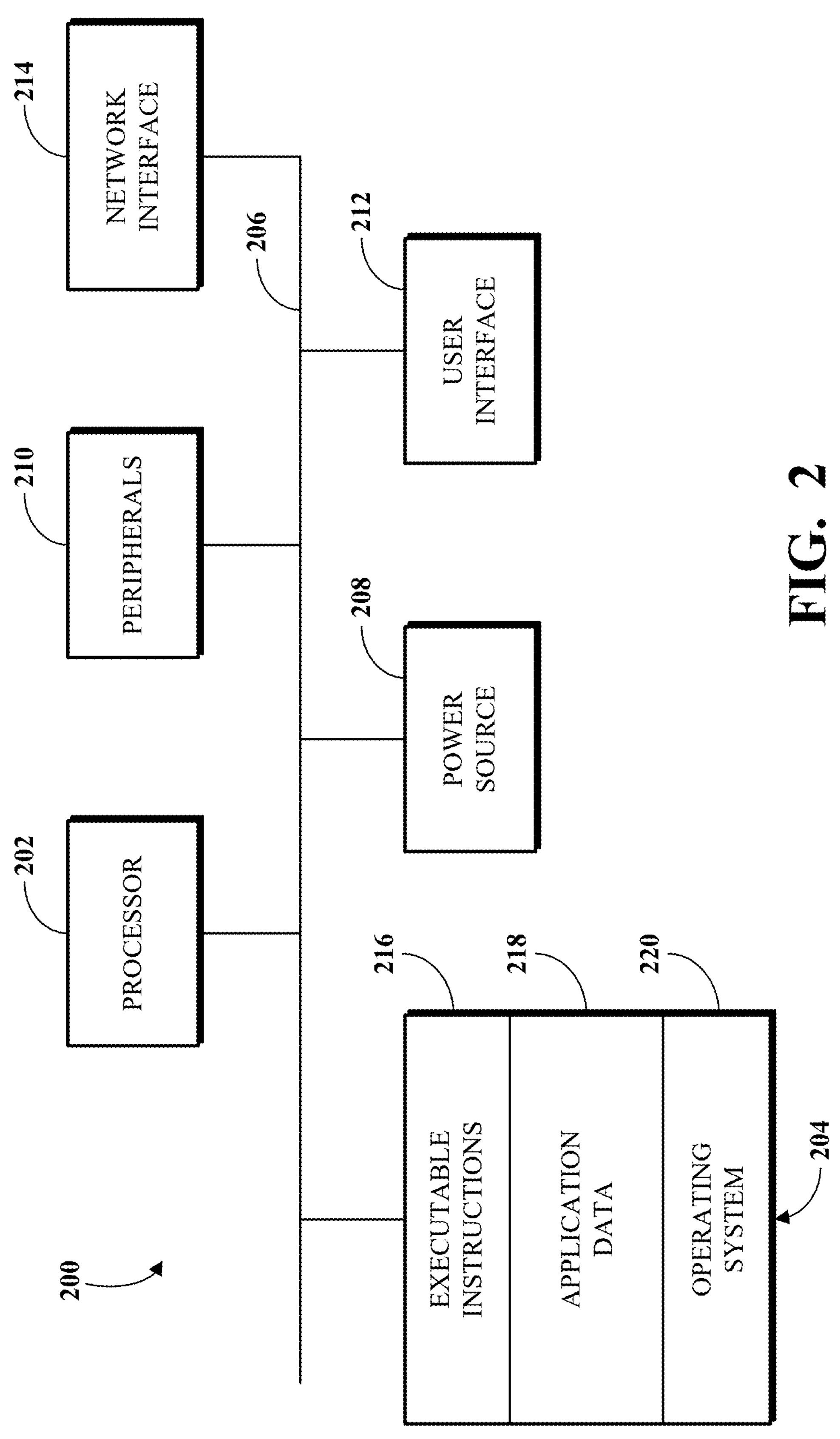
FIG. 2 is a block diagram of an example internal configuration of a computing device for facilitating removal of motion artifacts in a PPG signal.

FIG. 2 is a block diagram of an example internal configuration of a computing device 200 for removing motion artifacts in PPG signals. The computing device 200 may implement one or more aspects and/or components of the wearable device 108 of FIG. 1.

The computing device 200 includes components or units, such as a processor 202, a memory 204, a bus 206, a power source 208, peripherals 210, a user interface 212, a network interface 214, other suitable components, or a combination thereof. One or more of the memory 204, the power source 208, the peripherals 210, the user interface 212, or the network interface 214 can communicate with the processor 202 via the bus 206.

The processor 202 is a central processing unit (or another processing unit such as a graphics processing unit), such as a microprocessor, and can include single or multiple processors having single or multiple processing cores. Alternatively, the processor 202 can include another type of device, or multiple devices, configured for manipulating or processing information. For example, the processor 202 can include multiple processors interconnected in one or more manners, including hardwired or networked. The operations of the processor 202 can be distributed across multiple devices or units that can be coupled directly or across a local area or other suitable type of network. The processor 202 can include a cache, or cache memory, for local storage of operating data or instructions.

The memory 204 includes one or more memory components, which may each be volatile memory or non-volatile memory. For example, the volatile memory can be random access memory (RAM) (e.g., a dynamic random-access memory (DRAM) module, such as double data rate (DDR) synchronous DRAM). In another example, the non-volatile memory of the memory 204 can be a disk drive, a solid-state drive, flash memory, or phase-change memory. In some implementations, the memory 204 can be distributed across multiple devices. For example, the memory 204 can include network-based memory or memory in multiple clients or servers performing the operations of those multiple devices.

The memory 204 can include data for immediate access by the processor 202. For example, the memory 204 can include executable instructions 216, application data 218, and an operating system 220. The executable instructions 216 can include one or more application programs, which can be loaded or copied, in whole or in part, from non-volatile memory to volatile memory to be executed by the processor 202. For example, the executable instructions 216 can include instructions for performing some or all of the techniques of this disclosure. The application data 218 can include user data, database data (e.g., database catalogs or dictionaries), or the like. In some implementations, the application data 218 can include functional programs, such as a web browser, a web server, a database server, another program, or a combination thereof. The operating system 220, when present, can be, for example, Microsoft Windows®, Mac OS X®, or Linux®; an operating system for a mobile device, such as a smartphone or tablet device; or an operating system for a non-mobile device, such as a mainframe computer. For example, a target device that is an embedded device might not have an operating system.

The power source 208 provides power to the computing device 200. For example, the power source 208 can be an interface to an external power distribution system. In another example, the power source 208 can be a battery, such as where the computing device 200 is a mobile device or is otherwise configured to operate independently of an external power distribution system. In some implementations, the computing device 200 may include or otherwise use multiple power sources. In some such implementations, the power source 208 can be a backup battery.

The peripherals 210 includes one or more sensors, detectors, or other devices configured for monitoring the computing device 200 or the environment around the computing device 200. For example, the peripherals 210 can include a geolocation component, such as a global positioning system location unit. In another example, the peripherals can include a temperature sensor for measuring temperatures of components of the computing device 200, such as the processor 202. In another example, the peripherals can include a PPG sensor, such as the PPG sensor 104 of FIG. 1, and an accelerometer sensor, such as the accelerometer sensor 106 of FIG. 1. In some implementations, the computing device 200 can omit some or all of the peripherals 210.

The user interface 212 includes one or more input interfaces and/or output interfaces. An input interface may, for example, be a positional input device, such as a mouse, touchpad, touchscreen, or the like; a keyboard; or another suitable human or machine interface device. An output interface may, for example, be a display, such as a liquid crystal display, a cathode-ray tube, a light emitting diode display, virtual reality display, or other suitable display.

The network interface 214 provides a connection or link to a network (e.g., the network 112 shown in FIG. 1). The network interface 214 can be a wired network interface or a wireless network interface. The computing device 200 can communicate with other devices via the network interface 214 using one or more network protocols, such as using Ethernet, transmission control protocol (TCP), internet protocol (IP), power line communication, an IEEE 802.X protocol (e.g., Wi-Fi, Bluetooth, or ZigBee), infrared, visible light, general packet radio service (GPRS), global system for mobile communications (GSM), code-division multiple access (CDMA), Z-Wave, another protocol, or a combination thereof.

Figure 3:
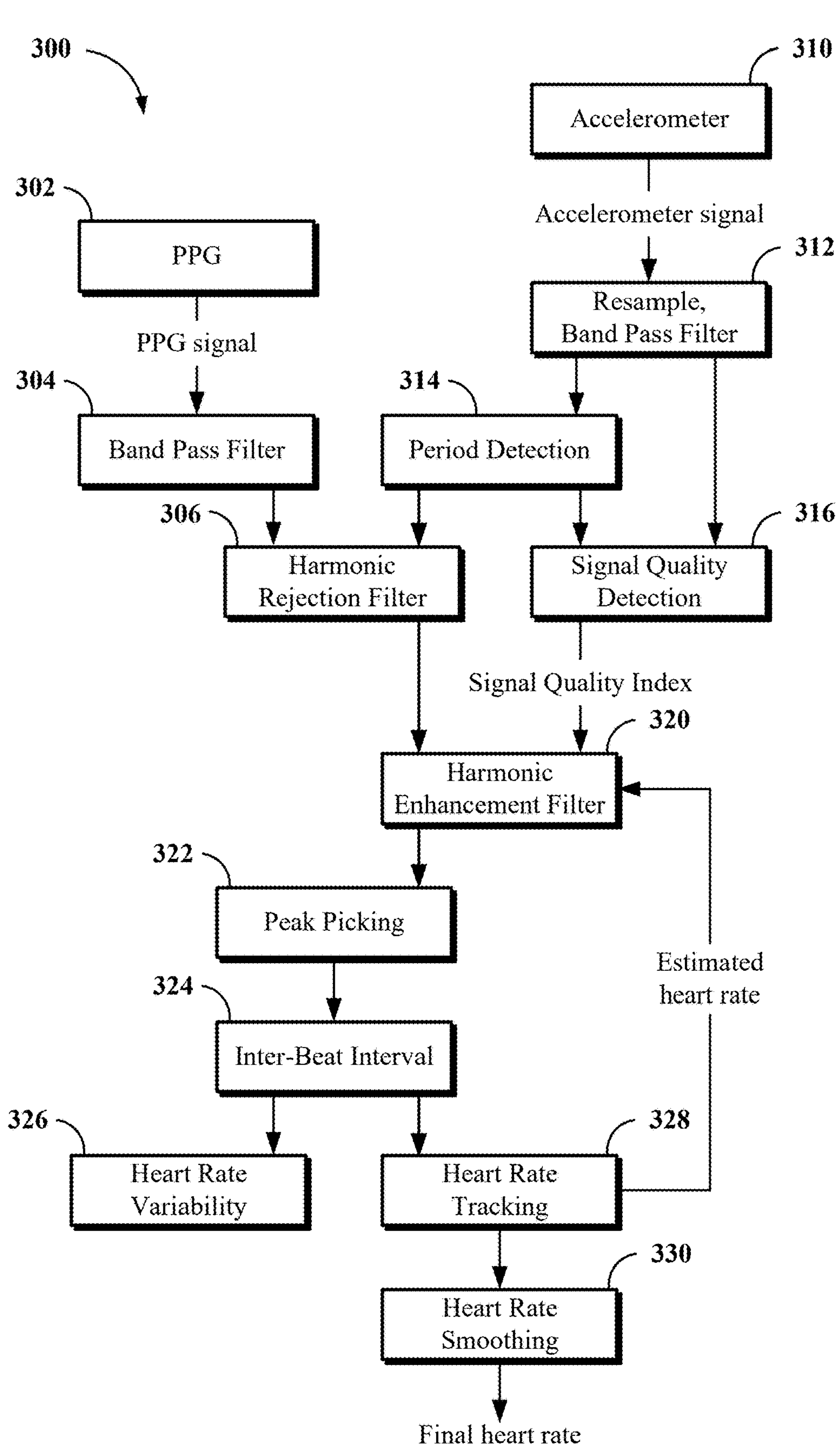
FIG. 3 is a block diagram of an example of a system for removing motion artifacts from a PPG signal.

FIG. 3 is a block diagram of an example of a system 300 for removing motion artifacts from a PPG signal. The system 300 may be implemented as a wearable device, such as the wearable device 108 of FIG. 1. Alternatively, the system 300 may be implemented at another computing device, which may include at least a portion of the components of the computing device 200. Some aspects of the system 300, implemented as a wearable device, may comprise hardware and/or software components implemented by one or more computing devices, such as instances of the computing device 200 of FIG. 2, that are not integral to the wearable device, such as remote servers, cloud servers, smartphones, tablets, computers, as so on.

The system 300 comprises a PPG sensor 302, which may be an instance of the PPG sensor 104 of FIG. 1, for detecting a raw heart-rate signal, labeled as "PPG signal" in FIG. 3, of a user, such as the user 102 of FIG. 1. The PPG signal is provided as input to a band pass filter 304, which comprises an electronic circuit and/or computer instructions executed by a processor for allowing signals within a specific frequency range to pass through while attenuating frequencies outside that range. In some embodiments, the specific range of frequencies to pass through include those corresponding to typical heart rates, such as 40 to 200 bpm. A purpose of the band pass filter 304 is to attenuate frequency components of the PPG signal that are ostensibly outside the frequency range of typical heart rates. The band pass filter 304 outputs a band-passed PPG signal. In some implementations, optimal cutoff frequencies of the band pass filter 304 can be found using a greedy algorithm or grid search similar to hyperparameter tuning that is found in some machine-learning algorithms.

The system 300 further comprises an accelerometer 310, which may be an instance of the accelerometer sensor 106 of FIG. 1, for detecting motions, labeled as "accelerometer signal" in FIG. 3, associated with the PPG sensor 302 and/or a user of the system 300, e.g., of a wearer of a wearable device implementing the system 300. The accelerometer signal is input to a resampler and band pass filter 312, where a resampler comprises an electronic circuit and/or computer instructions executed by a processor for upsampling or downsampling a first signal, in this case the accelerometer signal, to more closely match the sampling rate of a second signal, in this case the PPG signal. As described above, a band pass filter comprises an electronic circuit and/or computer instructions executed by a processor for allowing signals within a specific frequency range to pass through while attenuating frequencies outside that range. In some embodiments, the specific range of frequencies to pass through include those corresponding to typical motion artifacts, such as 20 to 200 cycles per minute. A purpose of the resampler and band pass filter 312 is to attenuate frequency components of the accelerometer signal that are ostensibly outside the frequency range of motion artifacts of interest.

In some embodiments, the accelerometer signal may consist of an acceleration along a single dimension, and in some embodiments, the accelerometer signal may comprise multiple axial and/or radial components, for example, an acceleration along some predefined x, y, and z axes. In the latter case, the components of the accelerometer signal may be combined into a single signal, such as by weighted average, geometric average, and so on.

The resampled and band-passed accelerometer signal is input to a period detector 314 for detecting, or determining, a period of the resampled and band-passed accelerometer signal. A period detector comprises an electronic circuit and/or computer instructions executed by a processor that measures and outputs the duration of one complete cycle of a periodic (or quasi-periodic) signal. In some embodiments, the period detector 314 observes the resampled and band-passed accelerometer signal over a predefined duration and determines an average period for that duration. In some embodiments, the period detector 314 may be a frequency detector, which detects, or determines, a frequency of the resampled and band-passed accelerometer signal. Because period and frequency are inversely related, determination of either a period or frequency necessarily indicates the inverse quantity; thus, the term period detector as used herein refers to a functional unit that determines either a period or a frequency.

The period (or frequency) of the resampled and band-passed accelerometer signal, determined by the period detector 314, is input to a harmonic notch filter 306 (e.g., a harmonic rejection filter) along with the band-passed PPG signal. In some embodiments, the harmonic notch filter 306 is defined by the following 2-tap FIR equation:

$$y_1[n] = x_1[n] - g_1 \cdot x_1[n - d_1],$$

n is an index based on a sampling rate of the PPG signal;

$y_1[n]$ corresponds to the filtered PPG signal that is output of the harmonic notch filter 306, which may be referred to herein as the first filtered PPG signal;

$x_1[n]$ corresponds to the band-passed PPG signal that is output from the band pass filter 304;

$d_1$ is a parameter that controls positions of filter notches and is based on the period of the motion artifacts as determined by the period detector 314;

$g_1$ is a coefficient that controls an amount of attenuation, which can be predefined or empirically determined; and the "1" subscripts are used to distinguish this first equation corresponding to the harmonic notch filter 306 from a second equation corresponding to a harmonic comb filter 320 described later herein.

Figure 6:
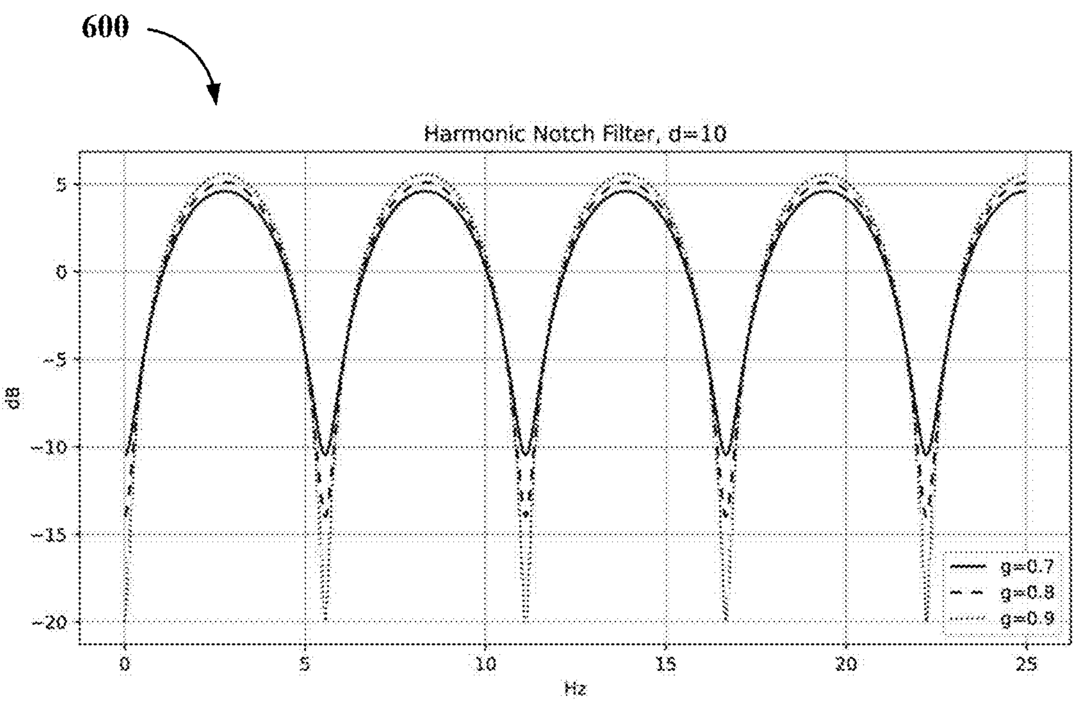
FIG. 6 is an example of a family of spectra of a harmonic notch filter.

FIG. 6 shows an example of a family of spectra 600 of the harmonic notch filter 306 with $d_1$=10 and $g_1$=0.7, 0.8, and 0.9.

For an N-tap harmonic notch filter, the above equation may be generalized as follows:

$$y_1[n] = a_1 \cdot x_1[n] - \sum_{i=1}^{N-1} g_1[i] \cdot x_1[n - i \cdot d_1],$$

$a_1$ is a scaling coefficient that can be predefined or empirically determined; and $g_1[i]$ is a vector of $g_1$ coefficients $g_1[1], g_1[2], \ldots g_1[N-1]$ indexed by i.

Returning to the resampler and band pass filter 312, the resampled and filtered accelerometer signal that is output therefrom is also input to a signal quality detector 316 for detecting, or determining, a quality of the resampled and filtered accelerometer signal, which may be referred to herein as a signal quality index, or SQI. If the resampled and filtered accelerometer signal has little activity (e.g., minimal motion artifacts), then the signal quality detector 316 outputs a high-magnitude value for the SQI. On the other hand, if the resampled and filtered accelerometer signal has a lot of activity (e.g., significant motion artifacts), then the signal quality detector 316 outputs a low-magnitude value for the SQI. In other words, the SQI indicates an amount of motion artifacts that may be present in the PPG signal and which would be advantageous to remove. In some implementations, the SQI can be determined as a function of a standard deviation of the accelerometer signal during an idle period, σidle, and a standard deviation of the accelerometer signal during an active period, σactive, as follows:

$$SQI = \sigma_{idle} / \sigma_{active}.$$

The SQI of the resampled and band-passed accelerometer signal, determined by the signal quality detector 316, is input to a harmonic comb filter 320 (e.g., a harmonic enhancement filter) along with the filtered PPG signal that is output by the harmonic notch filter 306. Additionally, an estimated heart rate, that is determined by a heart rate tracker 328 as described later herein, is input to the harmonic comb filter 320 as part of a feedback loop. In some embodiments, the harmonic comb filter 320 is defined by the following 2-tap IIR equation:

$$y_2[n] = x_2[n] - g_2 \cdot y_2[n - d_2],$$

n is an index based on a sampling rate of the PPG signal;

$y_2[n]$ corresponds to the enhanced PPG signal that is output of the harmonic comb filter 320, which may be referred to herein as the second filtered PPG signal;

$x_2[n]=y_1[n]$ and corresponds to the filtered PPG signal that is output from the harmonic notch filter 306;

$d_2$ is a parameter that controls positions of filter peaks and is based on the previous estimates of the heart rate as determined by the heart rate tracker 328;

$g_2$ is a coefficient that controls an amount of amplification and is inversely proportional to the SQI; and the "2" subscripts are used to distinguish this second equation corresponding to the harmonic comb filter 320 from the first equation corresponding to the harmonic notch filter 306 described earlier herein.

Figure 7:
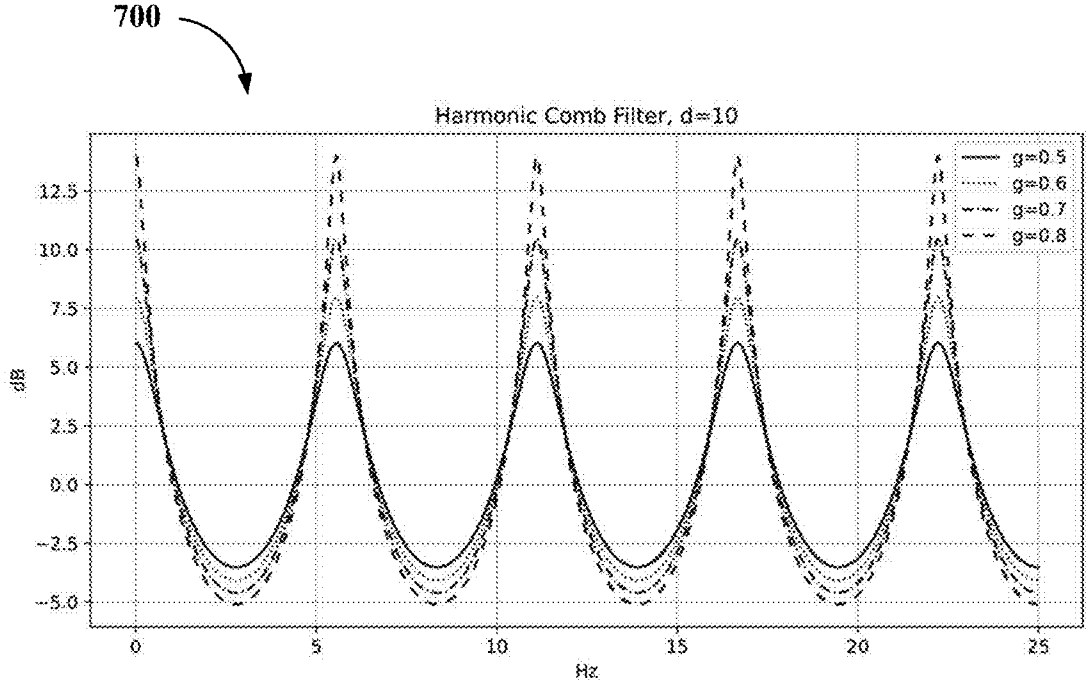
FIG. 7 is an example of a family of spectra of a harmonic comb filter.

FIG. 7 shows an example of a family of spectra 700 of the harmonic comb filter 320 with $d_2$=10 and $g_2$=0.5, 0.6, 0.7, and 0.8.

For an M-tap harmonic comb filter, the above equation may be generalized as follows:

$$y_2[n] = a_2 \cdot x_2[n] - \sum_{i=1}^{M-1} g_2[i] \cdot y_2[n - i \cdot d_2],$$

$a_2$ is a scaling coefficient that can be predefined or empirically determined; and $g_2[i]$ is a vector of $g_2$ coefficients $g_2[1], g_2[2], \ldots g_2[M-1]$ indexed by i.

In some embodiments, the coefficient $g_2$ can be determined according to the following process:

if SQI is greater than a predefined threshold, then $g_2=0$;

if SQI is less than or equal to the predefined threshold, then increase $g_2$ incrementally based on a confidence level of the estimated heart rate determined by the heart rate tracker 328, as explained later herein.

The enhanced PPG signal determined by the harmonic comb filter 320 is output to a peak picker 322 that identifies, or determines, the peaks (and/or troughs) of the enhanced PPG signal. A peak picker comprises an electronic circuit and/or computer instructions executed by a processor that identifies maximum and/or minimum amplitude points within a signal, in this case, in the enhanced PPG signal. The peaks of the enhanced PPG signal may comprise systolic peaks and/or diastolic peaks. In some embodiments, the peak picker 322 may implement aspects of a technique described in the following publication: Bishop SM, Ercole A, "Multi-Scale Peak and Trough Detection Optimised for Periodic and Quasi-Periodic Neuroscience Data," Acta Neurochir Suppl. 2018; 126:189-195; doi: 10.1007/978-3-319-65798-1_39; PMID: 29492559.

The identified peaks determined by the peak picker 322 are output to an inter-beat interval detector 324 for determining an inter-beat interval of the enhanced PPG signal. An inter-beat interval detector comprises an electronic circuit and/or computer instructions executed by a processor that determines durations between peaks (or troughs) of a signal, in this case, of the enhanced PPG signal. In some embodiments, an inter-beat interval (IBI) is a duration of time between adjacent equivalent peaks of the enhanced PPG signal, for example, between two systolic peaks or between two diastolic peaks. In some embodiments, the inter-beat interval detector 324 determines an inter-beat interval for every adjacent equivalent peak. In some implementations, the inter-beat interval detector 324 observes peaks within a predefined sliding window, for example, over an 8 second window of peaks of the enhanced PPG signal, and determines an average inter-beat interval over the sliding window.

The inter-beat interval detector 324 may include processing to remove outliers, such as IBIs beyond 3 standard deviations of a mean previously determined IBIs within a predefined sliding window (where the window may be infinite). The inter-beat interval detector 324 may additionally or alternatively include filtering, such as linear quadratic estimation (LQE), to determine the IBI more accurately. In some implementations, the LQE filter is a Kalman filter. For example, the IBI may be described by a state model, where the current ($n^{th}$) estimate of the IBI, IBI [n], equals the previously ($(n-1)^{th}$) estimate of the IBI, IBI [n−1], plus an observed noise variance, noise_var:

$$IBI[n] = IBI[n-1] + \text{noise\_var}.$$

The heart rate tracker 328 determines a pre-estimated heart rate based on the inter-beat interval determined by the inter-beat interval detector 324. In some embodiments, the pre-estimated heart rate (peHR, in units of bpm) is determined based on the inter-beat interval (in units of seconds) by the following equation:

$$peHR = 60/IBI.$$

The heart rate tracker 328 further determines a confidence vector, C, that comprises a plurality of candidate heart rates within a predefined range. As an example, the range of candidate heart rates may be from 50 to 180 bpm inclusive, and the confidence vector may consist of a quantity of equally spaced heart rates, such as 50, 55, 60, 65, . . . 180, or unequally spaced heart rates, such as 50, 65, 75, 80, 84, 86, 87, 88, 89, . . . 131, 132, 133, 134, 136, 140, 155, 180, where the spacing indicates one or more resolutions for the system 300 in determining a heart rate from the PPG signal. In some embodiments, the candidate heart rates may be integers, while in other embodiments the candidate heart rates may include fractions. The candidate heart rates of the confidence vector are the indices, k, into the confidence vector, where each kth candidate heart rate is associated with a confidence level, c[k], determined by the heart rate tracker 328.

The confidence vector may be initialized with predefined values for each confidence level, for example, all zeros. Thereafter, the confidence levels of individual candidate heart rates may be adjusted by the heart rate tracker 328 in several steps. One adjustment of the confidence vector consists of a decrease in confidence levels, and another adjustment of the confidence vector consists of an increase in confidence levels, both explained below.

The confidence level of each candidate heart rate in the confidence vector may be decreased over time such that each respective confidence level tends toward zero in the absence of the system 300 determining a pre-estimated heart rate that is close to the respective candidate heart rate. In some embodiments, this is implemented by periodically (or from time to time) by multiplying each respective confidence value by a forgetting factor, f, according to the following equation:

$$c[k]=c[k]*f;\ f<1.$$

The forgetting factor may be determined empirically.

The confidence levels of a quantity of candidate heart rates about the pre-estimated heart rate may be increased over time such that each respective confidence level of the quantity of confidence levels increases relative to other confidence levels of candidate heart rates that are not close to the pre-estimated heart rate. For example, the quantity of candidate heart rates about the pre-estimated heart rate may equal three, where the confidence level of the candidate heart rate that is closest to the pre-estimated heart rate may be increased by 1, the confidence level of the next-larger candidate heart rate may be increased by ½, and the confidence level of the next-smaller candidate heart rate may be increased by ½. This linear fall-off profile for increasing confidence levels may be partially generalized for the closest candidate heart rate, k, having confidence level c[k], for the next smaller candidate heart rate, k−1, having confidence level c[k−1], and for the next larger candidate heart rate, k+1, having confidence level c[k+1], where it is assumed for simplicity and without loss of generality that the candidate heart rates are equally spaced integers $k_{lowest}$, $k_{lowest}+1$, $k_{lowest}+2$, . . . k−1, k, k+1, . . . , $k_{highest}-1$, $k_{highest}$, as follows:

$$c[k-1]=c[k-1]+w/p;$$

$$c[k]=c[k]+w/q;\text{ and}$$

$$c[k+1]=c[k+1]+w/r;$$

where w is a confidence weight based on the SQI, w/p, w/q, w/r are respective weights for the respective confidence levels, p>1, q>1, and r≥1, and where w=1, p=r=2, and q=1 for the numerical example described earlier. In some implementations, the confidence weight w is directly proportional to the SQI, such that when SQI is high, w is high, and when SQI is low, w is low.

Further generalizing, but continuing the simplifying assumption that the candidate heart rates are integers separated by 1, a linear fall-off for increasing confidence levels for the candidate heart rates about the pre-estimated heart rate may be described as follows. For a quantity Q of candidate heart rates about the pre-estimated heart rate, where Q is preferably but not necessarily odd, the confidence level of the candidate heart rate, k, that is closest to the pre-estimated heart rate may be increased by a weight w, the respective confidence levels of the first removed larger and smaller candidate heart rates, k+1, may be increased by a respective weight w(1−1*2/(Q+1)); the respective confidence levels of the second removed larger and smaller candidate heart rates, k+2, may be increased by a respective weight w(1−2*2/(Q+1)); the respective confidence levels of the third removed larger and smaller candidate heart rates, k±3, may be increased by a respective weight w(1−3*2/(Q+1)); and the respective confidence levels of the $i^{th}$ removed larger and smaller candidate heart rates, k±i, may be increased by a respective weight w(1−|i|*2/(Q+1)). A numerical example is provided below:

$$\text{let } Q=7 \text{ and } w=1$$

$$\begin{aligned}
c[k] &= c[k]+w(1-|i|*2/(Q+1)) \\
&= c[k]+w(1-0*2/(7+1)) \\
&= c[k]+w \\
&= c[k]+1 \\
c[k\pm 1] &= c[k\pm 1]+w(1-|i|*2/(Q+1)) \\
&= c[k\pm 1]+w(1-|\pm 1|*2/(7+1)) \\
&= c[k\pm 1]+w(3/4) \\
&= c[k\pm 1]+3/4 \\
c[k\pm 2] &= c[k\pm 2]+w(1-|i|*2/(Q+1)) \\
&= c[k\pm 2]+w(1-|\pm 2|*2/(7+1)) \\
&= c[k\pm 2]+w(1/2) \\
&= c[k\pm 2]+1/2 \\
c[k\pm 3] &= c[k\pm 3]+w(1-|i|*2/(Q+1)) \\
&= c[k\pm 3]+w(1-|\pm 3|*2/(7+1)) \\
&= c[k\pm 2]+w(1/4) \\
&= c[k\pm 2]+1/4
\end{aligned}$$

Figure 4:
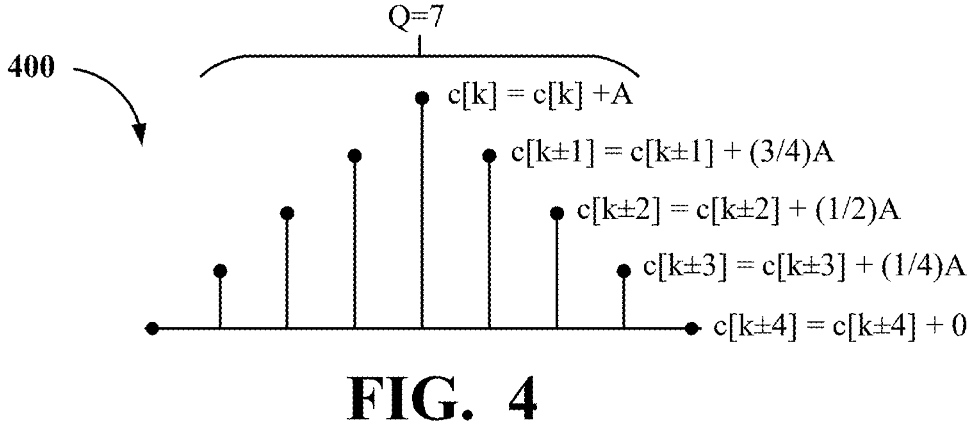
FIG. 4 is a depiction of a numerical example for a linear fall-off profile for increasing respective confidence levels for candidate heart rates about a pre-estimated heart rate.

FIG. 4 depicts the above numerical example for a linear fall-off profile 400 for increasing the confidence levels for the candidate heart rates about the pre-estimated heart rate. Note that FIG. 4 does not depict the values of the confidence levels themselves; rather, it depicts increases thereof. The quantity Q of candidate heart rates may be predefined, determined empirically, configurable by a user, and/or adaptable by the system. For example, the system 300 may adapt the quantity Q according to performance and/or power constraints.

Figure 5:
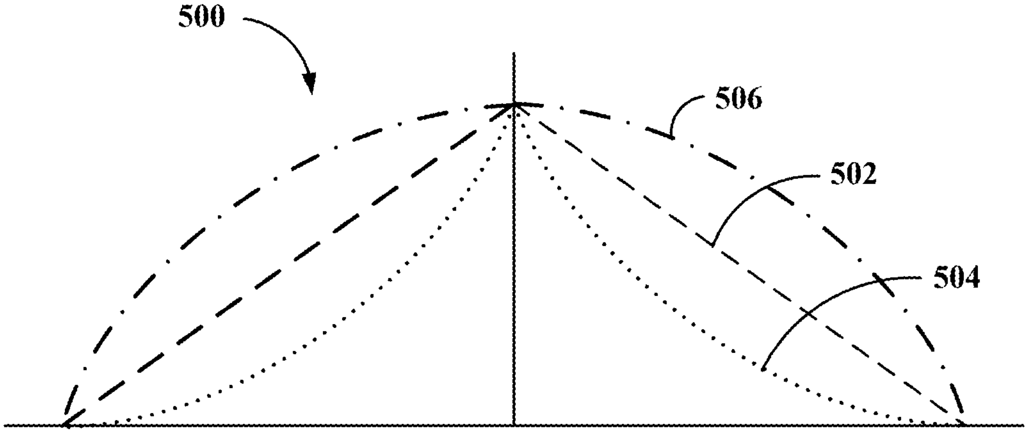
FIG. 5 is a depiction of several examples of various fall-off profiles for increasing the confidence levels, including an example of a linear fall-off profile, an exponential fall-off profile, and a polynomial fall-off profile.

Other suitable fall-off profiles for increasing the confidence levels about the pre-estimated heart rate may be utilized. FIG. 5 depicts some examples of various fall-off profiles 500 for increasing the confidence levels, including an example of a linear fall-off profile 502, an example of an exponential fall-off profile 504, and an example of a polynomial fall-off profile 506. Other fall-off profiles and/or asymmetric fall-off profiles are within the scope of this disclosure.

After adjusting the confidence levels of the confidence vector as described above—e.g., decreasing all confidence levels according to the forgetting factor and increasing the confidence levels of the quantity Q of candidate heart rates about the pre-estimated heart rate—the heart rate tracker 328 establishes as the estimated heart rate the candidate heart rate associated with the largest confidence level. The estimated heart rate can be considered a more refined version of the pre-estimated heart rate, where the estimated heart rate fluctuates less rapidly than the pre-estimated heart rate according to how the confidence levels in the confidence vector fluctuate. A heart rate tracker comprises an electronic circuit and/or computer instructions executed by a processor that refines the pre-estimated heart rate. The heart rate tracker 328 outputs this estimated heart rate to the harmonic comb filter 320 as described earlier. The heart rate tracker 328 also outputs this estimated heart rate to a heart rate smoother 330, which is described below.

The heart rate smoother 330 performs additional smoothing on the estimated heart rates to eliminate unlikely fluctuations in the estimated heart rates and ultimately determines a final heart rate. A heart rate smoother comprises an electronic circuit and/or computer instructions executed by a processor that smooths the estimated heart rate to determine a final heart rate. In some implementations, the heart rate smoother 330 may implement the following function:

$$HR_{smoothed} = HR_{previous} + \mu \cdot w \cdot (HR_{current} - HR_{previous}),$$

$HR_{smoothed}$ is the final heart rate, $HR_{previous}$ is an adjusted selected estimated heart rate of a previous evaluation window, $HR_{current}$ is the estimated heart rate prior to adjustment, μ is a smoothing factor that can be predefined of empirically determined, and w is the weight for the closest-matching candidate heart rate described above with respect to the heart rate tracker 328.

In some implementations, the evaluation window utilized by the heart rate smoother 330 is a sliding window having a duration and a time increment for "sliding," for example, the duration of the sliding window may be 8 seconds and the time increment may be 2 seconds.

Figure 8:
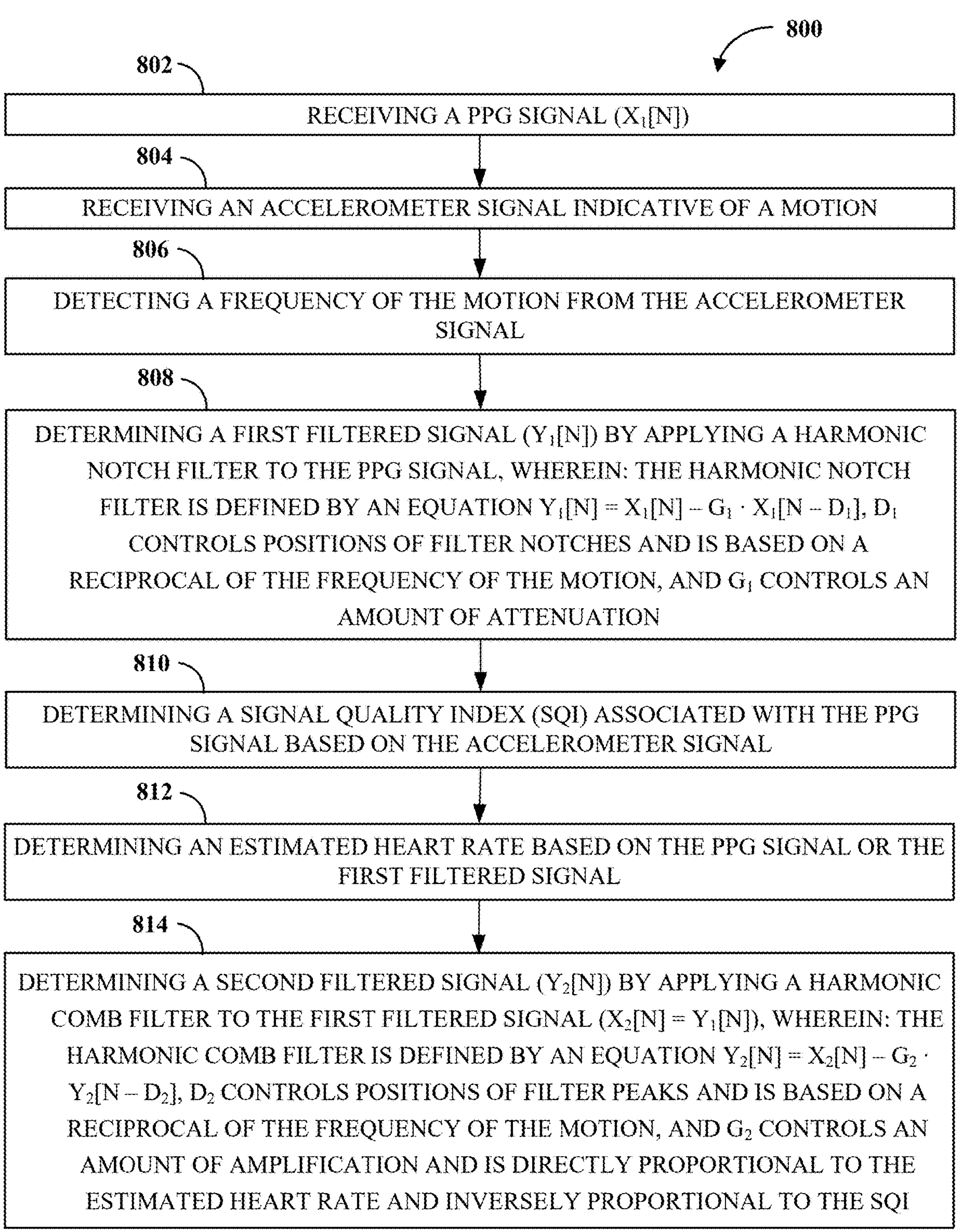
FIG. 8 is a flowchart of an example of a technique for removing motion artifacts in PPG signals.

To further describe some implementations in greater detail, reference is next made to an example of a technique 800 that may be performed by or using one or more computing devices for removing motion artifacts in PPG signals. FIG. 8 is a flowchart of an example of a technique for implementing removal of motion artifacts in PPG signals.

The technique 800 can be executed using computing devices, such as the systems, hardware, and software described or referenced with respect to FIGS. 1-7. The technique 800 can be performed, for example, by executing a machine-readable program or other computer-executable instructions, such as routines, instructions, programs, or other code. The steps, or operations, of the technique 800, or another technique, method, process, or algorithm described in connection with the implementations disclosed herein can be implemented directly in hardware, firmware, software executed by hardware, circuitry, or a combination thereof.

For simplicity of explanation, the technique 800 is depicted and described herein as a series of steps or operations. However, the steps or operations of the technique 800 in accordance with this disclosure can occur in various orders and/or concurrently. Additionally, other steps or operations not presented and described herein may be used. Furthermore, not all illustrated steps or operations may be required to implement a technique in accordance with the disclosed subject matter. The technique 800 may be performed by one or more computing devices, for example a wearable device, such as the wearable device 108 of FIG. 1, which may comprise one or more components, such as the PPG sensor 104 and the accelerometer sensor 106 of FIG. 1. The wearable device may include or communicate with other computing devices, which may comprise at least a processor, such as the processor 202, and a memory, sch as the memory 204 of FIG. 2.

The step 802 comprises receiving a PPG signal ($x_1[n]$). The PPG signal may be the PPG signal referred to in FIG. 3. The PPG signal may be detected or otherwise acquired by a PPG sensor, such as the PPG sensor 104 of FIG. 1. In some implementations, the PPG sensor is a component of a wearable computing device, such as the wearable device 108 of FIG. 1.

The step 804 comprises receiving an accelerometer signal indicative of a motion. The accelerometer signal may be the accelerometer signal referred to in FIG. 3. The accelerometer signal may be detected or otherwise acquired by an accelerometer sensor, such as the accelerometer sensor 106 of FIG. 1. In some implementations, the accelerometer sensor is a component of a wearable computing device, such as the wearable device 108 of FIG. 1. In some implementations, the PPG sensor and the accelerometer sensor are disposed on a same wearable device, such that the PPG sensor and the accelerometer sensor experience similar motion activity.

The step 806 comprises detecting a frequency of the motion from the accelerometer signal. Detecting the frequency, or the period, of the motion from the accelerometer signal may be performed by a period detector, such as the period detector 314 of FIG. 4. In some implementations, the frequency of the motion is within a range of 20 cycles per minute to 200 cycles per minute.

The step 808 comprises determining a first filtered signal ($y_1[n]$) by applying a harmonic notch filter to the PPG signal, wherein: the harmonic notch filter is defined by an equation $y_1[n]=x_1[n]-g_1 \cdot x_1[n-d_1]$, $d_1$ controls positions of filter notches and is based on a reciprocal of the frequency of the motion, and $g_1$ controls an amount of attenuation. The harmonic notch filter may be the harmonic notch filter 306 in FIG. 3. In some implementations, the harmonic notch filter is an F IR filter that may comprise more than two taps.

The step 810 comprises determining a signal quality index (SQI) associated with the PPG signal based on the accelerometer signal. The SQI may be the SQI referred to in FIG. 3 that is determined by the signal quality detector 316 of FIG. 3. In some implementations, the SQI is directly proportional to the accelerometer signal. In some implementations, the SQI is determined according to the following process: determining an idle standard deviation (@idle) from the accelerometer signal during a period of idle motion activity; determining an active standard deviation ($\sigma_{active}$) from the accelerometer signal during a period of active motion activity; and determining the SQI as a function of the idle standard deviation and the active standard deviation, the SQI is defined by an equation $SQI=\sigma_{idle}/\sigma_{active}$.

The step 812 comprises determining an estimated heart rate based on the PPG signal or the first filtered signal. The estimated heart rate may be the estimated heart rate referred to in FIG. 3 that is determined by the heart rate tracker 328 of FIG. 3.

In some implementations, the estimated heart rate is determined according to the following process: initializing a confidence level for each of a plurality of candidate heart rates within a predefined range; determining a pre-estimated heart rate based on the PPG signal or the first filtered signal; determining a set of identified candidate heart rates comprising a closest-matching candidate heart rate to the pre-estimated heart rate, a next-smaller candidate heart rate, and a next-larger candidate heart rate; calculating respective weights, based on the SQI, for the identified heart rates; adjusting the confidence levels for the identified candidate heart rates by applying the respective weights; and selecting, as the estimated heart rate, the candidate heart rate having a largest adjusted confidence level.

In some implementations, the confidence levels for the identified heart rates are determined according to the following process: computing, for the confidence level ($c[k-1]$) of the next-smaller identified candidate heart rate ($k-1$), $c[k-1]=c[k-1]+w/p$; computing, for the confidence level ($c[k]$) of the closest-matching identified candidate heart rate (k), c[k]=c[k]+w/q; and computing, for the confidence level (c[k±1]) of the next-larger identified candidate heart rate (k+1), c[k±1]=c[k±1]+w/r; wherein w/p, w/q, w/r are the respective weights, p≥1, q≥1, and r≥1. In some implementations, p=r; and p<q. In some implementations, p=r=2; and q=1.

In some implementations, the estimated heart rate is determined according to the following process: initializing a confidence level for each of a plurality of candidate heart rates within a predefined range; determining a pre-estimated heart rate based on the PPG signal or the first filtered signal; determining an odd quantity Q of candidate heart rates comprising a closest-matching candidate heart rate (k) to the pre-estimated heart rate, (Q−1)/2 next-smaller candidate heart rates (k−1, k−2, . . . k−(Q−1)/2), and (Q−1)/2 next-larger candidate heart rates (k+1, k±2, . . . k+(Q−1)/2); adjusting the confidence level of each identified heart rate (c[k−i], i=[−(Q−1)/2, . . . 1, 0, 1, . . . (Q−1)/2]) according to a linear fall-off profile c[k±i]=c[k±i]+w(1−|i|*2(Q−1), wherein w is based on the SQI and w>0; and selecting, as the estimated heart rate, the candidate heart rate having a largest adjusted confidence level.

The step 814 comprises determining a second filtered signal ($y_2[n]$) by applying a harmonic comb filter to the first filtered signal ($x_2[n]=y_1[n]$), wherein: the harmonic comb filter is defined by an equation $y_2[n]=x_2[n]-g_2 \cdot y_2[n-d_2]$, $d_2$ controls positions of filter peaks and is based on a reciprocal of previous estimate of the heart rate, and $g_2$ controls an amount of amplification and is inversely proportional to the SQI. The harmonic comb filter may be the harmonic comb filter 320 in FIG. 3. In some implementations, the harmonic comb filter is an IIR filter that may comprise more than two taps.

In some implementations, a final heart rate may be determined by adjusting the selected estimated heart rate using a smoothing function based on the selected estimated heart rate, a previously selected estimated heart rate, and the weight for the closest-matching candidate heart rate.

In some implementations, a final heart rate may be determined by adjusting the estimated heart rate using a smoothing function defined by an equation $HR_{smoothed}=HR_{previous}+\mu \cdot W \cdot (HR_{current}-HR_{previous})$, wherein: $HR_{smoothed}$ is the final heart rate, $HR_{previous}$ is an adjusted estimated heart rate of a previous evaluation window, $HR_{current}$ is the estimated heart rate prior to adjustment, μ is a smoothing factor, and w is the weight for the closest-matching candidate heart rate.

In some implementations, a final heart rate may be determined by identifying peaks and troughs of the second filtered signal; determining a set of inter-beat intervals (IBIs) based on the identified peaks and troughs; determining a reduced set of IBIs by removing outlier IBIs whose respective values exceed a predefined quantity of standard deviations of the set of IBIs above or below a mean of the set of IBIs; determining a current estimate ($IBI_{current}$) of the IBIs using a state model defined by an equation $IBI_{current}=IBI_{previous}+\text{noise}$, wherein $IBI_{previous}$ is a previous estimate of the IBI and noise represents observation noise; and determining a final heart rate ($HR_{final}$), in beats per minute, according to an equation $HR_{final}=60/IBI_{current}$.

Some implementations of removing motion artifacts from PPG signals disclosed herein include a method, comprising: receiving a PPG signal ($x_1[n]$); receiving an accelerometer signal indicative of a motion; detecting a frequency of the motion from the accelerometer signal; determining a first filtered signal ($y_1[n]$) by applying a harmonic notch filter to the PPG signal, wherein: the harmonic notch filter is defined by an equation $$y_1[n] = a_1 \cdot x_1[n] - \sum_{i=1}^{N-1} g_1[i] \cdot x_1[n - i \cdot d_1],$$

$d_1$ controls positions of filter notches and is based on a reciprocal of the frequency of the motion, and each $g_1[i]$ controls an amount of attenuation; determining a signal quality index (SQI) associated with the PPG signal based on the accelerometer signal; determining an estimated heart rate based on the PPG signal or the first filtered signal; determining a second filtered signal ($y_2[n]$) by applying a harmonic comb filter to the first filtered signal ($x_2[n]=y_1[n]$), wherein: the harmonic comb filter is defined by an equation $$y_2[n] = a_2 \cdot x_2[n] - \sum_{i=1}^{M-1} g_2[i] \cdot y_2[n - i \cdot d_2],$$

$d_2$ controls positions of filter peaks and is based on a reciprocal of the frequency of the motion, and each $g_2[i]$ controls an amount of amplification and is directly proportional to the estimated heart rate and inversely proportional to the SQI.

In some implementations, N=2; and M=2.

In some implementations, the SQI is directly proportional to the accelerometer signal.

In some implementations, the method further comprises determining the estimated heart rate by: initializing a confidence level for each of a plurality of candidate heart rates within a predefined range; determining a pre-estimated heart rate based on the PPG signal or the first filtered signal; determining a set of identified candidate heart rates comprising a closest-matching candidate heart rate to the pre-estimated heart rate, a next-smaller candidate heart rate, and a next-larger candidate heart rate; calculating respective weights, based on the SQI, for the identified heart rates; adjusting the confidence levels for the identified candidate heart rates by applying the respective weights; and selecting, as the estimated heart rate, the candidate heart rate having a largest adjusted confidence level.

In some implementations, the method further comprises: determining a final heart rate by adjusting the estimated heart rate using a smoothing function based on the estimated heart rate, a previously selected estimated heart rate, and the weight for the closest-matching candidate heart rate.

In some implementations, the method further comprises: determining a final heart rate by adjusting the selected estimated heart rate using a smoothing function defined by an equation $HR_{smoothed}=HR_{previous}+\mu \cdot w \cdot (HR_{current}-HR_{previous})$, wherein: $HR_{smoothed}$ is the final heart rate, $HR_{previous}$ is an adjusted selected estimated heart rate of a previous evaluation window, HR current is the estimated heart rate prior to adjustment, μ is a smoothing factor, and w is the weight for the closest-matching candidate heart rate.

In some implementations, the method further comprises adjusting the confidence levels for the identified candidate heart rates by: computing, for the confidence level (c[k−1]) of the next-smaller identified candidate heart rate (k−1), c[k−1]=c[k−1]+w/p; computing, for the confidence level (c[k]) of the closest-matching identified candidate heart rate (k), c[k]=c[k]+w/q; and computing, for the confidence level (c[k±1]) of the next-larger identified candidate heart rate $(k+1)$, $c[k\pm 1]=c[k\pm 1]+w/r$; wherein w/p, w/q, w/r are the respective weights, $p\geq 1$, $q\geq 1$, and $r\geq 1$.

In some implementations, p=r; and p<q.

In some implementations, p=r=2; and q=1.

In some implementations, the method further comprises: receiving the PPG signal from a PPG sensor disposed on a wearable device; and receiving the accelerometer signal from an accelerometer sensor disposed on the wearable device.

In some implementations, the method further comprises determining the estimated heart rate by: initializing a confidence level for each of a plurality of candidate heart rates within a predefined range; determining a pre-estimated heart rate based on the PPG signal or the first filtered signal; determining an odd quantity Q of candidate heart rates comprising a closest-matching candidate heart rate (k) to the pre-estimated heart rate, (Q−1)/2 next-smaller candidate heart rates (k−1, k−2, . . . k−(Q−1)/2), and (Q−1)/2 next-larger candidate heart rates (k+1, k±2, . . . k± (Q−1)/2); adjusting the confidence level of each identified heart rate (c[k−i], i=[−(Q−1)/2, . . . 1, 0, 1, . . . (Q−1)/2]) according to a linear fall-off profile c[k±i]=c[k±i]+w(1−[i] *2(Q−1), wherein w is based on the SQI and w>0; and selecting, as the estimated heart rate, the candidate heart rate having a largest adjusted confidence level.

In some implementations, the method further comprises: determining an idle standard deviation ($\sigma_{idle}$) from the accelerometer signal during a period of idle motion activity; determining an active standard deviation ($\sigma_{active}$) from the accelerometer signal during a period of active motion activity; and determining the SQI as a function of the idle standard deviation and the active standard deviation, the SQI is defined by an equation $SQI=\sigma_{idle}/\sigma_{active}$.

In some implementations, the method further comprises: identifying peaks and troughs of the second filtered signal; determining a set of inter-beat intervals (IBIs) based on the identified peaks and troughs; determining a reduced set of IBIs by removing outlier IBIs whose respective values exceed a predefined quantity of standard deviations of the set of IBIs above or below a mean of the set of IBIs; determining a current estimate ($IBI_{current}$) of the IBIs using a state model defined by an equation $IBI_{current}=IBI_{previous}+$ noise, wherein $IBI_{previous}$ is a previous estimate of the IBI and noise represents observation noise; and determining a final heart rate ($HR_{final}$), in beats per minute, according to an equation $HR_{final}=60/IBI_{current}$.

Some implementations of removing motion artifacts from PPG signals disclosed herein include a system, comprising: one or more memories; and one or more processors configured to execute instructions stored in the one or more memories to: receive a PPG signal ($x_1[n]$); receive an accelerometer signal indicative of a motion; detect a frequency of the motion from the accelerometer signal; determine a first filtered signal ($y_1[n]$) by applying a harmonic notch filter to the PPG signal, wherein: the harmonic notch filter is defined by an equation $$y_1[n] = a_1 \cdot x_1[n] - \sum_{i=1}^{N-1} g_1[i] \cdot x_1[n - i \cdot d_1],$$

$d_1$ controls positions of filter notches and is based on a reciprocal of the frequency of the motion, and each $g_1[i]$ controls an amount of attenuation; determine a signal quality index (SQI) associated with the PPG signal based on the accelerometer signal; determine an estimated heart rate based on the PPG signal or the first filtered signal; determine a second filtered signal ($y_2[n]$) by applying a harmonic comb filter to the first filtered signal ($x_2[n]=y_1[n]$), wherein: the harmonic comb filter is defined by an equation $$y_2[n] = a_2 \cdot x_2[n] - \sum_{i=1}^{M-1} g_2[i] \cdot y_2[n - i \cdot d_2],$$

$d_2$ controls positions of filter peaks and is based on a reciprocal of the frequency of the motion, and each $g_2[i]$ controls an amount of amplification and is directly proportional to the estimated heart rate and inversely proportional to the SQI.

In some implementations, the one or more processors are configured to execute the instructions to: initialize a confidence level for each of a plurality of candidate heart rates within a predefined range; determine a pre-estimated heart rate based on the PPG signal or the first filtered signal; determine a set of identified candidate heart rates comprising a closest-matching candidate heart rate to the pre-estimated heart rate, a next-smaller candidate heart rate, and a next-larger candidate heart rate; calculate respective weights, based on the SQI, for the identified heart rates; adjust the confidence levels for the identified candidate heart rates by applying the respective weights; and select, as the estimated heart rate, the candidate heart rate having a largest adjusted confidence level.

In some implementations, the system includes a wearable device and the one or more processors are configured to execute the instructions to: receive the PPG signal from a PPG sensor disposed on the wearable device; and receive the accelerometer signal from an accelerometer sensor disposed on the wearable device.

In some implementations, the one or more processors are configured to execute the instructions to: determine an idle standard deviation ($\sigma_{idle}$) from the accelerometer signal during a period of idle motion activity; determine an active standard deviation ($\sigma_{active}$) from the accelerometer signal during a period of active motion activity; and determine the SQI as a function of the idle standard deviation and the active standard deviation, the SQI is defined by an equation $SQI=\sigma_{idle}/\sigma_{active}$.

Some implementations of removing motion artifacts from PPG signals disclosed herein include a non-transitory computer-readable medium storing instructions operable to cause one or more processors to perform operations comprising: receiving a PPG signal ($x_1[n]$); receiving an accelerometer signal indicative of a motion; detecting a frequency of the motion from the accelerometer signal; determining a first filtered signal ($y_1[n]$) by applying a harmonic notch filter to the PPG signal, wherein: the harmonic notch filter is defined by an equation $$y_1[n] = a_1 \cdot x_1[n] - \sum_{i=1}^{N-1} g_1[i] \cdot x_1[n - i \cdot d_1],$$

$d_1$ controls positions of filter notches and is based on a reciprocal of the frequency of the motion, and each $g_1[i]$ controls an amount of attenuation; determining a signal quality index (SQI) associated with the PPG signal based on the accelerometer signal; determining an estimated heart rate based on the PPG signal or the first filtered signal; determining a second filtered signal ($y_2[n]$) by applying a harmonic comb filter to the first filtered signal ($x_2[n]=y_1[n]$), wherein: the harmonic comb filter is defined by an equation $$y_2[n] = a_2 \cdot x_2[n] - \sum_{i=1}^{M-1} g_2[i] \cdot y_2[n - i \cdot d_2],$$

$d_2$ controls positions of filter peaks and is based on a reciprocal of the frequency of the motion, and each $g_2[i]$ controls an amount of amplification and is directly proportional to the estimated heart rate and inversely proportional to the SQI.

In some implementations, the operations further comprise: initializing a confidence level for each of a plurality of candidate heart rates within a predefined range; determining a pre-estimated heart rate based on the PPG signal or the first filtered signal; determining a set of identified candidate heart rates comprising a closest-matching candidate heart rate to the pre-estimated heart rate, a next-smaller candidate heart rate, and a next-larger candidate heart rate; calculating respective weights, based on the SQI, for the identified heart rates; adjusting the confidence levels for the identified candidate heart rates by applying the respective weights; and selecting, as the estimated heart rate, the candidate heart rate having a largest adjusted confidence level.

In some implementations, the operations further comprise: determining an idle standard deviation ($\sigma_{idle}$) from the accelerometer signal during a period of idle motion activity; determining an active standard deviation ($\sigma_{active}$) from the accelerometer signal during a period of active motion activity; and determining the SQI as a function of the idle standard deviation and the active standard deviation, the SQI is defined by an equation $SQI=\sigma_{idle}/\sigma_{active}$.

The implementations of this disclosure can be described in terms of functional block components and various processing operations. Such functional block components can be realized by a number of hardware or software components that perform the specified functions. For example, the disclosed implementations can employ various integrated circuit components (e.g., memory elements, processing elements, logic elements, look-up tables, and the like), which can carry out a variety of functions under the control of one or more microprocessors or other control devices. Similarly, where the elements of the disclosed implementations are implemented using software programming or software elements, the systems and techniques can be implemented with a programming or scripting language, such as C, C++, Java, JavaScript, assembler, or the like, with the various algorithms being implemented with a combination of data structures, objects, processes, routines, or other programming elements.

Functional aspects can be implemented in algorithms that execute on one or more processors. Furthermore, the implementations of the systems and techniques disclosed herein could employ a number of conventional techniques for electronics configuration, signal processing or control, data processing, and the like. The words "mechanism" and "component" are used broadly and are not limited to mechanical or physical implementations, but can include software routines in conjunction with processors, etc. Likewise, the terms "system" or "tool" as used herein and in the figures, but in any event based on their context, may be understood as corresponding to a functional unit implemented using software, hardware (e.g., an integrated circuit, such as an application specific integrated circuit (ASIC)), or a combination of software and hardware. In certain contexts, such systems or mechanisms may be understood to be a processor-implemented software system or processor-implemented software mechanism that is part of or callable by an executable program, which may itself be wholly or partly composed of such linked systems or mechanisms.

Implementations or portions of implementations of the above disclosure can take the form of a computer program product accessible from, for example, a computer-usable or computer-readable medium. A computer-usable or computer-readable medium can be a device that can, for example, tangibly contain, store, communicate, or transport a program or data structure for use by or in connection with a processor. The medium can be, for example, an electronic, magnetic, optical, electromagnetic, or semiconductor device.

Other suitable mediums are also available. Such computer-usable or computer-readable media can be referred to as non-transitory memory or media, and can include volatile memory or non-volatile memory that can change over time. The quality of memory or media being non-transitory refers to such memory or media storing data for some period of time or otherwise based on device power or a device power cycle. A memory of an apparatus described herein, unless otherwise specified, does not have to be physically contained by the apparatus, but is one that can be accessed remotely by the apparatus, and does not have to be contiguous with other memory that might be physically contained by the apparatus.

This document may reference a specific number of things (e.g., "six mobile devices"). Unless explicitly set forth otherwise, the numbers provided are examples only and may be replaced with any positive integer, integer or real number, as would make sense for a given situation. For example, "six mobile devices" may, in alternative embodiments, include any positive integer number of mobile devices. Unless otherwise mentioned, an object referred to in singular form (e.g., "a computer" or "the computer") may include one or multiple objects (e.g., "the computer" may refer to one or multiple computers).

As used herein, unless explicitly stated otherwise, any term specified in the singular may include its plural version. For example, "a computer that stores data and runs software," may include a single computer that stores data and runs software or two computers-a first computer that stores data and a second computer that runs software. Also "a computer that stores data and runs software," may include multiple computers that together stored data and run software. At least one of the multiple computers stores data, and at least one of the multiple computers runs software.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for removing motion artifacts in photoplethysmography (PPG) signals, comprising:

receiving a PPG signal;

receiving an accelerometer signal indicative of a motion;

detecting a frequency of the motion from the accelerometer signal;

determining a band-passed PPG signal based on applying a band pass filter to the PPG signal;

determining a first filtered signal by applying a harmonic notch filter to the band-passed PPG signal, wherein the harmonic notch filter is based on a notch position control parameter, and an attenuation control coefficient, wherein the notch position control parameter controls positions of filter notches and is based on a reciprocal of the frequency of the motion, and wherein the attenuation control coefficient controls an amount of attenuation;

determining a signal quality index (SQI) associated with the PPG signal based on the accelerometer signal;

determining, using a heart rate tracker, an estimated heart rate based on the PPG signal or the first filtered signal;

determining a second filtered signal by applying a harmonic comb filter to the first filtered signal determined based on application of the harmonic notch filter to the band-passed PPG signal, wherein the harmonic comb filter is based on a peak position control parameter and an amplification control coefficient, wherein the peak position control parameter controls positions of filter peaks and is based on a reciprocal of the estimated heart rate, and wherein the amplification control coefficient controls an amount of amplification and is inversely proportional to the SQI; and determining a final heart rate based on the second filtered signal and a smoothing function based on the estimated heart rate.

2. The method of claim 1, wherein:

the SQI is directly proportional to the accelerometer signal.

3. The method of claim 1, further comprising determining the estimated heart rate by:

initializing a confidence level for each of a plurality of candidate heart rates within a predefined range;

determining a pre-estimated heart rate based on the PPG signal or the first filtered signal;

determining a set of identified candidate heart rates comprising a closest-matching candidate heart rate to the pre-estimated heart rate, a next-smaller candidate heart rate, and a next-larger candidate heart rate;

calculating respective weights, based on the SQI, for the identified heart rates;

adjusting the confidence levels for the identified candidate heart rates by applying the respective weights; and selecting, as the estimated heart rate, a candidate heart rate having a largest adjusted confidence level.

4. The method of claim 3, further comprising:

determining the final heart rate by adjusting the estimated heart rate using the smoothing function based on the estimated heart rate, a previously selected estimated heart rate, and a weight for the closest-matching candidate heart rate.

5. The method of claim 3, further comprising:

determining the final heart rate by adjusting the selected estimated heart rate using the smoothing function, wherein the smoothing function generates the final heart rate based on smoothing an adjusted selected estimated heart rate of a previous evaluation window based on the estimated heart rate prior to adjustment, a smoothing factor, and a weight for the closest-matching candidate heart rate.

6. The method of claim 3, further comprising adjusting the confidence levels for the identified candidate heart rates by:

computing, for a confidence level of a next-smaller identified candidate heart rate;

computing, for a confidence level of a closest-matching identified candidate heart rate; and computing, for a confidence level of a next-larger identified candidate heart rate.

7. The method of claim 1, further comprising:

receiving the PPG signal from a PPG sensor disposed on a wearable device; and receiving the accelerometer signal from an accelerometer sensor disposed on the wearable device.

8. The method of claim 1, further comprising determining the estimated heart rate by:

initializing a confidence level for each of a plurality of candidate heart rates within a predefined range;

determining a pre-estimated heart rate based on the PPG signal or the first filtered signal;

determining an odd quantity of candidate heart rates comprising a closest-matching candidate heart rate to the pre-estimated heart rate, next-smaller candidate heart rates, and next-larger candidate heart rates;

adjusting the confidence level of each identified heart rate according to a linear fall-off profile; and selecting, as the estimated heart rate, a candidate heart rate having a largest adjusted confidence level.

9. The method of claim 1, further comprising:

determining an idle standard deviation from the accelerometer signal during a period of idle motion activity;

determining an active standard deviation from the accelerometer signal during a period of active motion activity; and determining the SQI as a function of the idle standard deviation and the active standard deviation.

10. The method of claim 1, wherein determining the final heart rate based on the second filtered signal comprises:

identifying peaks and troughs of the second filtered signal;

determining a set of inter-beat intervals (IBIs) based on the identified peaks and troughs;

determining a reduced set of IBIs by removing outlier IBIs whose respective values exceed a predefined quantity of standard deviations of the set of IBIs above or below a mean of the set of IBIs;

determining a current estimate ($IBI_{current}$) of the IBIs using a state model the state model is based on a previous estimate of an IBI and an observation noise; and determining the final heart rate ($HR_{final}$), in beats per minute based on the current estimate ($IBI_{current}$).

11. A system, comprising:

one or more memories; and one or more processors configured to execute instructions stored in the one or more memories to:

receive a PPG signal;

receive an accelerometer signal indicative of a motion;

detect a frequency of the motion from the accelerometer signal;

determine a band-passed PPG signal based on applying a band pass filter to the PPG signal;

determine a first filtered signal by applying a harmonic notch filter to the band-passed PPG signal, wherein the harmonic notch filter is based on a notch position control parameter and an attenuation control coefficient, wherein the notch position control parameter controls positions of filter notches and is based on a reciprocal of the frequency of the motion, and wherein the attenuation control coefficient controls an amount of attenuation;

determine a signal quality index (SQI) associated with the PPG signal based on the accelerometer signal;

determine, using a heart rate tracker, an estimated heart rate based on the PPG signal or the first filtered signal;

determine a second filtered signal by applying a harmonic comb filter to the first filtered signal determined based on application of the harmonic notch filter to the band-passed PPG signal, wherein the harmonic comb filter is based on a peak position control parameter and an amplification control coefficient, wherein the peak position control parameter controls positions of filter peaks and is based on a reciprocal of the estimated heart rate, and wherein the amplification control coefficient controls an amount of amplification and is inversely proportional to the SQI; and determine a final heart rate based on the second filtered signal and a smoothing function based on the estimated heart rate.

12. The system of claim 11, wherein the instructions to determine the estimated heart rate includes instructions to:

initialize a confidence level for each of a plurality of candidate heart rates within a predefined range;

determine a pre-estimated heart rate based on the PPG signal or the first filtered signal;

determine a set of identified candidate heart rates comprising a closest-matching candidate heart rate to the pre-estimated heart rate, a next-smaller candidate heart rate, and a next-larger candidate heart rate;

calculate respective weights, based on the SQI, for the identified heart rates;

adjust the confidence levels for the identified candidate heart rates by applying the respective weights; and select, as the estimated heart rate, a candidate heart rate having a largest adjusted confidence level.

13. The system of claim 11, wherein the system includes a wearable device and the one or more processors are configured to execute the instructions to:

receive the PPG signal from a PPG sensor disposed on the wearable device; and receive the accelerometer signal from an accelerometer sensor disposed on the wearable device.

14. The system of claim 11, wherein the one or more processors are configured to execute the instructions to:

determine an idle standard deviation from the accelerometer signal during a period of idle motion activity;

determine an active standard deviation from the accelerometer signal during a period of active motion activity; and determine the SQI as a function of the idle standard deviation and the active standard deviation.

15. A non-transitory computer-readable medium storing instructions operable to cause one or more processors to perform operations comprising:

receiving a PPG signal;

receiving an accelerometer signal indicative of a motion;

detecting a frequency of the motion from the accelerometer signal;

determining a band-passed PPG signal based on applying a band pass filter to the PPG signal;

determining a first filtered signal by applying a harmonic notch filter to the band-passed PPG signal, wherein the harmonic notch filter is based on a notch position control parameter and an attenuation control coefficient, wherein the notch position control parameter controls positions of filter notches and is based on a reciprocal of the frequency of the motion, and wherein the attenuation control coefficient controls an amount of attenuation;

determining a signal quality index (SQI) associated with the PPG signal based on the accelerometer signal;

determining, using a heart rate tracker, an estimated heart rate based on the PPG signal or the first filtered signal;

determining a second filtered signal by applying a harmonic comb filter to the first filtered signal determined based on application of the harmonic notch filter to the band-passed PPG signal, wherein the harmonic comb filter is based on a peak position control parameter and an amplification control coefficient, wherein the peak position control parameter controls positions of filter peaks and is based on a reciprocal of the estimated heart rate, and wherein the amplification control coefficient controls an amount of amplification and is inversely proportional to the SQI; and determining a final heart rate based on the second filtered signal and a smoothing function based on the estimated heart rate.

16. The non-transitory computer-readable medium of claim 15, wherein the operations for determining the estimated heart rate further comprises:

initializing a confidence level for each of a plurality of candidate heart rates within a predefined range;

determining a pre-estimated heart rate based on the PPG signal or the first filtered signal;

determining a set of identified candidate heart rates comprising a closest-matching candidate heart rate to the pre-estimated heart rate, a next-smaller candidate heart rate, and a next-larger candidate heart rate;

calculating respective weights, based on the SQI, for the identified heart rates;

adjusting the confidence levels for the identified candidate heart rates by applying the respective weights; and selecting, as the estimated heart rate, a candidate heart rate having a largest adjusted confidence level.

17. The non-transitory computer-readable medium of claim 15, wherein the operations further comprise:

determining an idle standard deviation from the accelerometer signal during a period of idle motion activity;

determining an active standard deviation from the accelerometer signal during a period of active motion activity; and determining the SQI as a function of the idle standard deviation and the active standard deviation.

* * * * *